(12) United States Patent
Johnson et al.

(10) Patent No.: US 9,943,466 B1
(45) Date of Patent: Apr. 17, 2018

(54) BIOCOMPATIBLE DENTAL PUTTY FORMULATIONS FOR CONTROLLED RELEASE OF BUPIVACAINE

(71) Applicants: Research Triangle Institute, Research Triangle Park, NC (US); The University of North Carolina at Chapel Hill, Chapel Hill, NC (US)

(72) Inventors: Leah Marie Johnson, Durham, NC (US); Ginger Denison Rothrock, Cary, NC (US); Sarah Dorothy Shepherd, Raleigh, NC (US); Sandra Cordel O'Buckley, Durham, NC (US); Andrea Gail Neely, Durham, NC (US)

(73) Assignees: Research Triangle Institute, Research Triangle Park, NC (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/622,238

(22) Filed: Jun. 14, 2017

Related U.S. Application Data

(60) Provisional application No. 62/503,683, filed on May 9, 2017.

(51) Int. Cl.
| | |
|---|---|
| *A61K 9/16* | (2006.01) |
| *A61K 6/00* | (2006.01) |
| *A61K 9/00* | (2006.01) |
| *A61K 47/42* | (2017.01) |

(52) U.S. Cl.
CPC .......... *A61K 6/0067* (2013.01); *A61K 6/0002* (2013.01); *A61K 9/0002* (2013.01); *A61K 9/1647* (2013.01); *A61K 47/42* (2013.01); *A61K 2300/00* (2013.01)

(58) Field of Classification Search
CPC ....................................................... A61K 9/16
See application file for complete search history.

(56) References Cited

U.S. PATENT DOCUMENTS

| | | | |
|---|---|---|---|
| 5,618,563 A * | 4/1997 | Berde | A61K 9/1641 424/499 |
| 5,696,101 A | 12/1997 | Wu et al. | |
| 5,700,485 A | 12/1997 | Berde et al. | |
| 6,699,908 B2 | 3/2004 | Sackler et al. | |
| 8,523,569 B2 | 9/2013 | Neshat | |

(Continued)

OTHER PUBLICATIONS

American Society of Anesthesiologists, "Practice Guidelines for Acute Pain Management in the Perioperative Setting—An Updated Report by the American Society of Anesthesiologists Task Force on Acute Pain Management", "Anesthesiology", 2012, pp. 248-273, vol. 116, No. 2.

(Continued)

*Primary Examiner* — Carlos A Azpuru
(74) *Attorney, Agent, or Firm* — Hultquist, PLLC; Steven J. Hultquist

(57) ABSTRACT

The disclosure provides biocompatible dental material that is moldable and biodegradable and provides sustained and/or controlled delivery of one or more local anesthetics within a dental cavity or space. Such dental material is customizable for the size and shape needed for a particular patient or particular application. The dental material may also provide customizable sustained and/or controlled delivery of one or more local anesthetics.

30 Claims, 8 Drawing Sheets

(56) References Cited

U.S. PATENT DOCUMENTS

| | | | |
|---|---|---|---|
| 2003/0185872 A1 | 10/2003 | Kochinke | |
| 2007/0104769 A1 | 5/2007 | Feng et al. | |
| 2016/0089335 A1 | 3/2016 | Ohri et al. | |

OTHER PUBLICATIONS

Becker, D., "Pain Management: Part 1: Managing Acute and Postoperative Dental Pain", "Anesth Prog", 2010, pp. 67-79.

Boogaerts, J., et al., "Toxicity of Bupivacaine Encapsulated into Liposomes and Injected Intravenously: Comparison with Plain Solutions", "Anesthesia and analgesia", 1993, pp. 553-555, vol. 76.

Bramlett, K., et al., "A randomized, double-blind, dose-ranging study comparing wound infiltration of DepoFoam bupivacaine, an extended-release liposomal bupivacaine, to bupivacaine HCI for postsurgical analgesia in total knee arthroplasty", "The Knee", 2012, pp. 530-536, vol. 19.

Cheung, E., et al., "Rationalizing the Structural Properties of Bupivacaine BaseA Local AnestheticDirectly from Powder X-ray Diffraction Data", "Journal of Pharmaceutical Sciences", Mar. 2004, pp. 667-674, vol. 93, No. 3.

Coulthard, P., et al., "Pain control with paracetamol from a sustained release formulation and a standard release formulation after third molar surgery: a randomised controlled trial", "British Dental Journal", Sep. 22, 2001, pp. 319-334, vol. 191, No. 6.

Dhakar, R., et al., "From Formulation Variables to Drug Entrapment Efficiency of Microspheres: A Technical Review", "Journal of Drug Delivery & Therapeutics", 2012, pp. 128-133, vol. 2, No. 6.

D'Souza, S., et al., "Methods to Assess in Vitro Drug Release from Injectable Polymeric Particulate Systems", "Pharmaceutical Research", Mar. 2006, pp. 460-474, vol. 23, No. 3.

Golovanevski, L. et al., "In vivo study of an extended release bupivacaine formulation following site-directed nerve injection", "Journal of Bioactive and Compatible Polymers", 2014, pp. 114-125, vol. 30, No. 1.

Grant, G., et al., "DRV Liposomal Bupivacaine: Preparation, Characterization, and In Vivo Evaluation in Mice", "Pharmaceutical Research", 2001, pp. 336-343, vol. 18, No. 3.

Hu, D., et al., "Pharmacokinetic Profile of Liposome Bupivacaine Injection Following a Single Administration at the Surgical Site", "Clinical Drug Investigation", 2013, pp. 109-115, vol. 33.

Lambrechts, M., et al., "Liposomal extended-release bupivacaine for postsurgical analgesia", "Patient Preference and Adherence", 2013, pp. 885-890, vol. 7.

Le Corre, P., et al., "Preparation and characterization of bupivacaine-loaded polylactide and polylactide-co-glycolide microspheres", "International journal of pharmaceutics", 1994, pp. 41-49, vol. 107.

Le Corre, P., et al., "In vitro controlled release kinetics of local anaesthetics from poly(D,L-lactide) and poly(lactide-co-glycolide) microspheres", "Journal of microencapsulation", 1997, pp. 243-255, vol. 14.

Le Corre, P., et al., "Spray-dryed bupivacaine-loaded microspheres: in vitro evaluation and biopharmaceutics of bupivacaine following brachial plexus administration in sheep", "International Journal of Pharmaceutics", 2002, pp. 191-203, vol. 238.

Lee, S., et al., "Controlled delivery of a hydrophilic drug from a biodegradable microsphere system by supercritical anti-solvent precipitation technique", "Journal of microencapsulation", Nov. 2006, pp. 741-749, vol. 23, No. 7.

Masters, D., et al., "Prolonged Regional Nerve Blockade by Controlled Release of Local Anesthetic from a Biodegradable Polymer Matrix", "Anesthesiology", 1993, pp. 340-346, vol. 79.

Menhinick, K. A., et al., "The efficacy of pain control following nonsurgical root canal treatment using ibuprofen or a combination of ibuprofen and acetaminophen in a randomized, double-blind, placebo-controlled study", "International Endodontic Journal", 2004, pp. 531-541, vol. 37.

Mowat, J., et al., "Liposomal bupivacaine. Extended duration nerve blockade using large unilamellar vesicles that exhibit a proton gradient", "Anesthesiology", 1996, pp. 635-643, vol. 85, No. 3.

Paudel, K., et al., "Challenges and opportunities in dermal/transdermal delivery", "Therapeutic delivery", Jul. 2010, pp. 1-30, vol. 1.

Pek, Y.S., et al., "Sustained release of bupivacaine for post-surgical pain relief using coreshell microspheres", "Journal of Materials Chemistry B", 2014, pp. 8194-8200, vol. 2.

Saraghi, M. et al., "Three Newly Approved Analgesics: An Update", "Anesthesia progress", 2013, pp. 178-187, vol. 60.

Shikanov, A., et al., "Long acting local anestheticpolymer formulation to prolong the effect of analgesia", "Journal of Controlled Release", 2007, pp. 97-103, vol. 117.

Tarighi, P., et al., "A review on common chemical hemostatic agents in restorative dentistry", "Dental Research Journal", Jul.-Aug. 2014, pp. 423-428, vol. 11, No. 4.

Tsuchiya, Y., et al., "Thermal Decomposition Products of Poly(vinyl Alcohol)", "Journal of Polymer Science: Part A-1", 1969, pp. 3151-3158, vol. 7.

Weiniger, C.F., et al., "Extended release formulations for local anaesthetic agents", "Anaesthesia", 2012, pp. 906-916, vol. 67.

Zhang, H., et al., "Bupivacaine-loaded biodegradable poly(lactic-co-glycolic) acid microspheres I. Optimization of the drug incorporation into the polymer matrix and modelling of drug release", "International Journal of Pharmaceutics", 2008, pp. 244-249, vol. 351.

Note: For the non-patent literature citation that no month of publication is indicated, the year of publication is more than 1 year prior to the effective filing date of the present application.

\* cited by examiner

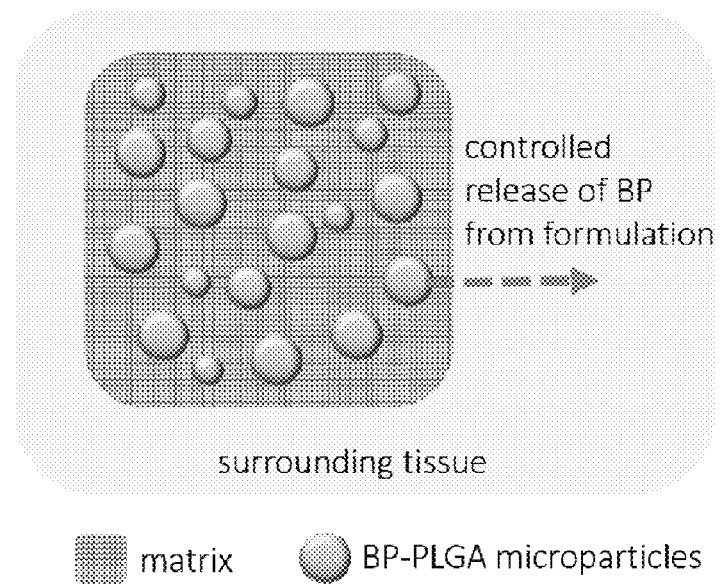
FIG. 1
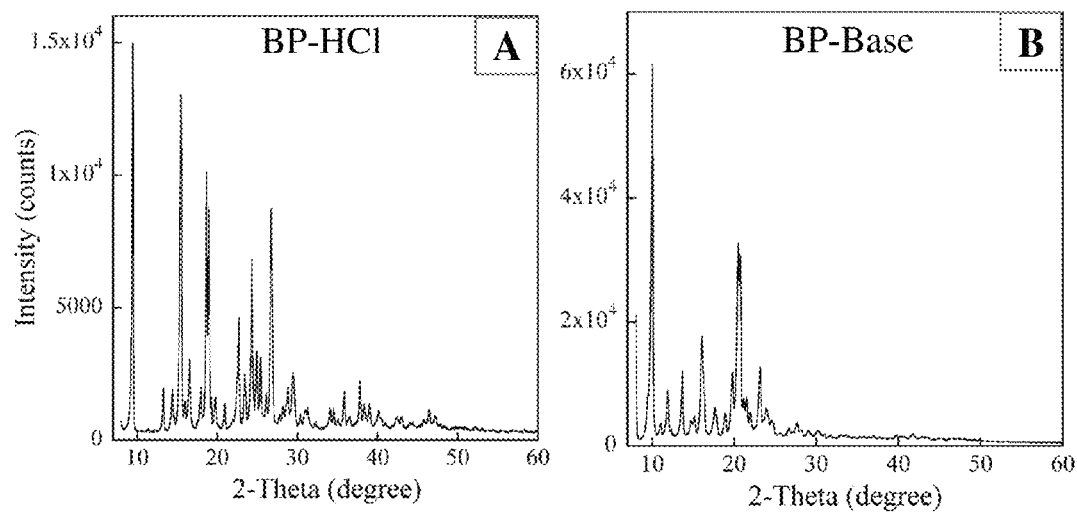
FIG. 2A          FIG. 2B

BIOCOMPATIBLE DENTAL PUTTY FORMULATIONS FOR CONTROLLED RELEASE OF BUPIVACAINE

CROSS-REFERENCE TO RELATED APPLICATIONS

This application claims the benefit of U.S. Provisional Application 62/503,683, filed May 9, 2017 and entitled "FORMULATIONS FOR CONTROLLED RELEASE OF BUPIVACAINE." The disclosure of U.S. Provisional Application 62/503,683 is hereby incorporated by reference in its entirety, for all purposes.

GOVERNMENT RIGHTS IN THE INVENTION

This invention was made with government support under the National Center for Advancing Translational Sciences (NCATS), National Institutes of Health, Grant Award Number 1UL1TR001111. The government has certain rights in the invention.

FIELD

The present disclosure relates to formulations providing controlled and/or sustained release of local anesthetic materials, particularly for post-operative dental pain and healing. The formulations are biodegradable and allow customized placement of local anesthetics in a dental socket or dental space, for example, after a tooth extraction.

DESCRIPTION OF THE RELATED ART

The management of post-operative dental pain is imperative to eliminate needless patient suffering, improve health-related quality of life, and reduce health care costs resulting from additional clinical visits. Post-surgical dental pain is typically treated with orally administered analgesics that block inflammatory mediators (e.g., non-steroidal anti-inflammatory drugs, corticosteroids) or block central mechanisms of pain perception (e.g., opioids). Although extremely beneficial for managing pain, these orally delivered drugs require continuous self-medication by the patient, and hold potential for adverse systemic effects, which may result in sleep disruption, nausea, neurological and/or respiratory dysfunction, circulatory depression, and addiction.

Alternatively, anesthetic drugs or agents that block peripheral nerve impulses, such as bupivacaine, are delivered locally to the affected surgical site, thereby lessening the quantity of necessary postoperative analgesics and mitigating the deleterious effects of oral medications. A significant limitation of local anesthetics involves the short duration of efficacy, with most drugs lasting less than eight hours. This approach is unfavorable, as direct injection of anesthetic drugs often results in systemic absorption, reducing the ability of the drug to interact with targeted nerve cells. For instance, a single injection of bupivacaine results in a maximum plasma drug concentration within 30-45 minutes, with complete elimination after approximately 6-8 hours.

Efforts involving co-administration of vasoconstrictors fail to substantially extend the duration of drug efficacy and may also result in complications. Sustained delivery of local anesthetics may improve dental pain management by prolonging drug effectiveness, and reducing toxicity by slowing drug uptake into systemic circulation.

Accordingly, there is a need in the art for formulations and methods capable of sustained and/or controlled delivery of local anesthetics in conjunction with dental procedures.

SUMMARY

The present disclosure relates to biocompatible formulations for sustained and/or controlled release of local anesthetics such as bupivacaine. The biocompatible formulations comprise a moldable dental putty useful for customized placement of local anesthetics, for example, in an extraction site after dental extraction.

In one aspect, the disclosure relates to a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent.

In another aspect, the disclosure relates to a pain management system configured to be positioned in a dental extraction cavity in a patient after dental surgery comprising a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent.

In a further aspect, the disclosure relates to a method of providing controlled release of a local anesthetic at a tooth extraction site in a patient in need of said local anesthetic, comprising molding into a desired shape and size a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent; and applying the biocompatible dental putty to the tooth extraction site in the patient.

In another aspect, the disclosure relates to a method of controlling pain in a patient after a tooth extraction comprising molding into a desired shape and size a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent; and applying the biocompatible dental putty to the tooth extraction site in the patient.

Other aspects, features and embodiments of the invention will be more fully apparent from the ensuing disclosure and appended claims.

BRIEF DESCRIPTION OF THE DRAWINGS

FIG. 1 is a schematic illustrating an exemplary sustained release formulation for management of dental pain. The formulation comprising bupivacaine-poly-(lactic-co-glycolic) acid (BP-PLGA) microparticles embedded in a biodegradable hemostat matrix is placed within a dental cavity or socket. BP is controllably released from the PLGA microparticles, diffusing through the hemostat matrix, and entering the surrounding tissue.

FIG. 2A is an XRD profile of BP-HCl. FIG. 2B is an XRD profile of BP-base.

DETAILED DESCRIPTION

Figures 3A, 3B, 3C, 3D:
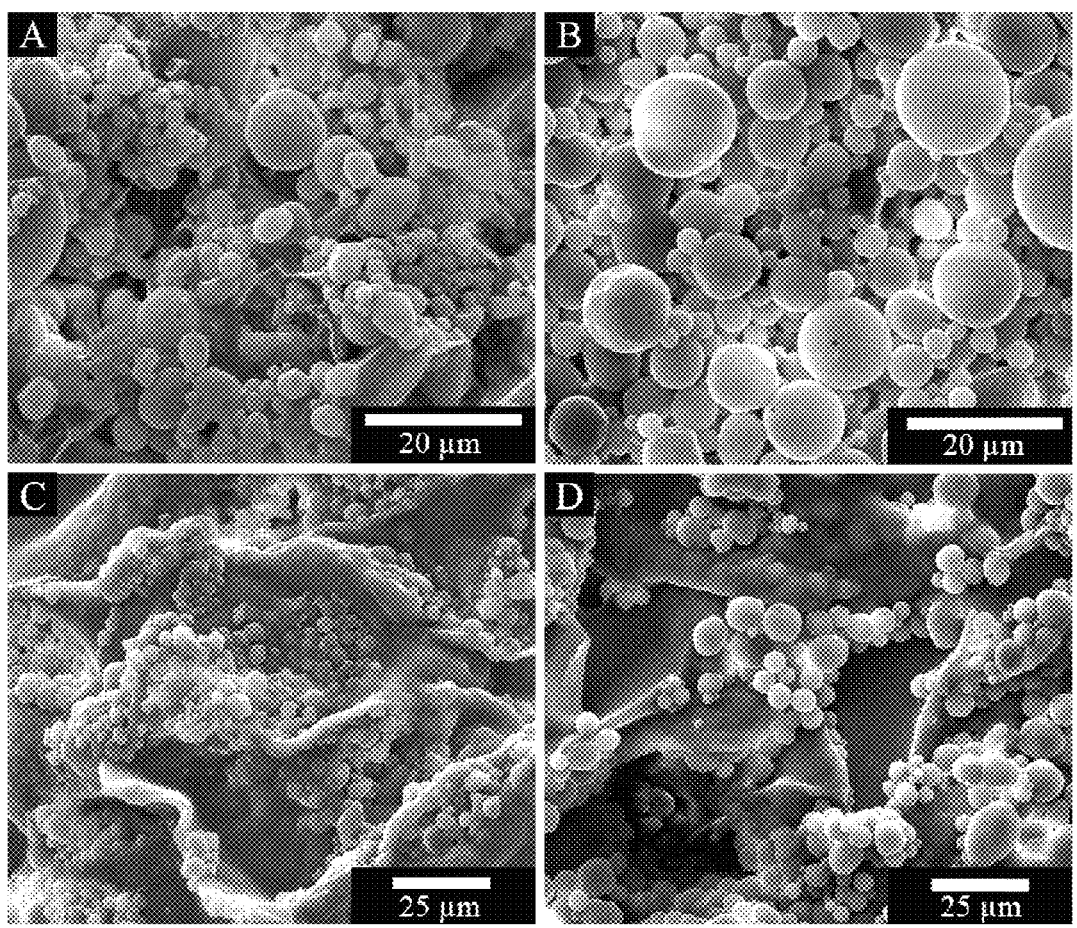
FIGS. 3A-3D are SEM images of drug-free PLGA microparticles (FIG. 3A), BP-PLGA microparticles (FIG. 3B), drug-free PLGA microparticles+Gelfoam® (FIG. 3C), and (FIG. 3D) BP-PLGA microparticles+Gelfoam® (FIG. 3C).

As used herein and in the appended claims, the singular forms "a", "and", and "the" include plural referents unless the context clearly dictates otherwise. Like numbers refer to like elements throughout.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure correspondingly contemplates such features, aspects and embodiments, or a selected one or ones thereof, in various permutations and combinations, as being within the scope of the present disclosure.

The present disclosure generally relates to a biocompatible dental material that is moldable and biodegradable and provides sustained and/or controlled delivery of one or more local anesthetics within a dental cavity or space. Such dental material is customizable for the size and shape needed for a particular patient or particular application. The dental material may also provide customizable sustained and/or controlled delivery of one or more local anesthetics.

Sustained delivery of local anesthetics for management of post-operative dental pain requires formulations that support oral healing while releasing drug in a controlled manner over a targeted dosing period. Current approaches for achieving sustained duration of anesthetic typically involve co-formulation of drug with a biocompatible polymeric carrier, which serves to control drug release kinetics. For example, anesthetics with extended release profiles for various clinical applications include liposomal suspensions, polymeric implants, injectable pastes, sustained release oral pills, and biocompatible microspheres. Many of these extended release formulations have proven successful, such as the FDA-approved EXPAREL®, a bupivacaine liposomal injection used for postsurgical pain control. In other examples, topical creams such as Emla® (lidocaine/prilocaine) and SonoPrep® (lidocaine) are also FDA-approved for dermal anesthesia.

Continued advancement of anesthetic delivery systems requires consideration of specific clinical needs. For treatment of post-operative dental pain following tooth extraction, a formulation according to the disclosure that simultaneously serves as a hemostatic agent and as a vehicle for controlled and/or sustained anesthetic delivery is highly advantageous. Current anesthetic delivery systems that include pills or injectable/implantable forms are incapable of serving as a hemostat for packing a dental cavity or socket. Similarly, hemostatic agents currently in the clinic do not offer the capability to deliver pain medications. Accordingly, a pain management system including a biocompatible dental material was developed that combines a moldable and biodegradable/absorbable hemostatic agent with local anesthetic drug or agent to control dental pain and support healing, for example, after a tooth extraction.

The dental material (putty) of the present disclosure comprises a soft, malleable paste or gel, has a putty consistency and can be molded to a desirable shape. In certain embodiments, therefore, a biocompatible dental putty is provided comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent, for example, into surrounding tissue.

As used herein, "local anesthetic" refers to those local anesthetics which can be used in conjunction with oral/dental surgery, especially for the extraction of teeth. Typically, such local anesthetics are injected but as described in the present disclosure the local anesthetics are formulated for sustained and/or controlled release and work in a substantially topical manner "Local anesthetic," "local anesthetic agent" and "local anesthetic drug" are used interchangeably and refer to any substance capable of providing local numbness, local insensitivity to pain, and/or analgesia and which can be used in conjunction with oral/dental surgery, for example, the extraction of teeth.

Exemplary local anesthetics include bupivacaine, mepivacaine, articaine, ropivacaine, dibucaine, etidocaine, tetracaine, lidocaine, prilocaine, and the like including mixtures and/or salts and/or derivatives thereof. In certain embodiments, the local anesthetic is bupivacaine or a salt thereof. Certain of the compounds disclosed herein may exist as stereoisomers including optical isomers. The scope of the disclosure includes all stereoisomers in both the racemic mixtures of such stereoisomers as well as the individual enantiomers which may be separated according to methods that are well known to those of ordinary skill in the art. By way of example, levobupivacaine, the (S)-(−) enantiomer of bupivacaine, may be used in the biocompatible dental putty of the disclosure.

The range of materials for use in the biocompatible dental putty of the disclosure may be constrained by the requirements for biocompatibility, flexibility and high anesthetic agent permeability. The dental material or putty according to the disclosure will comprise biocompatible materials known for or capable of use in the body. The biocompatible material preferably will not interfere with delivery of the local anesthetic agent and will not unintentionally degrade during manufacture and transport.

As used herein, "biodegradable" means that the material degrades in vivo over time. The period of time may be selected based on the particular material and use thereof and includes materials that are bioerodible or bioabsorbable such that the material is absorbed into the body of the patient.

As used herein, the term "controlled release" indicates a formulation prepared for a particular release profile of anesthetic agent over time. Typically, a controlled release formulation will also provide sustained release of an anesthetic agent over time. "Sustained release" indicates a prolongation of the duration of release and/or duration of action of an anesthetic agent. Both sustained release and controlled release contemplates continuous release of the local anesthetic agent until degradation of the materials from which the biocompatible dental putty was formed. The biocompatible dental putty of the disclosure may be formulated for sustained release or controlled release or both.

In certain embodiments, the biocompatible dental putty will provide a biphasic release profile wherein the release rate is higher for a period time, for example, the first 24 hours, and then the release rate will taper off. Such biphasic release is particularly suitable for controlling pain after a tooth extraction since it provides higher dosing immediately post-surgery and less dosing of the local anesthetic as the pain subsides after surgery.

The biodegradable microparticles, in aspects of the disclosure, comprise a polymeric material capable of releasing a local anesthetic agent encapsulated therein to obtain controlled and/or sustained release of the local anesthetic agent. Such release in the context of the disclosure may ultimately be into the oral tissue of a patient in the region of an extraction cavity.

Polymer materials for achieving a controlled and/or sustained release include polyanhydrides, copolymers of lactic acid and glycolic acid, poly(lactic) acid, poly(glycolic) acid, polycaprolactone, polyesters, polyorthoesters, proteins, polysaccharides and/or combinations thereof. The polymers should further be biodegradable so that manual removal from the placement site in a patient's body is avoided. Further, the materials must be biocompatible and compatible with local anesthetics.

In certain embodiments, the biodegradable microparticles comprise poly(lactic-co-glycolic acid) (PLGA). The poly(lactic-co-glycolic acid) may include polylactic acid and glycolic acid at a ratio of about 50:50 to about 75:25. In embodiments, the MW may be 7-17 kDa.

The biodegradable microparticles encapsulating local anesthetic agent may be prepared by methods known in the art, such as phase separation, fluidized bed coating, spray drying, supercritical fluids technology, or solvent evaporation, among others. By way of example, PLGA microparticles containing local anesthetic such as bupivacaine (BP) may be prepared by spray drying, supercritical fluids technology, or solvent evaporation. The choice of method depends on the physicochemical properties of selected drug, requirements for efficiency of encapsulation, ease of methodology, scale-up, and cost. In one nonlimiting example, a PLGA particle is prepared via solvent evaporation using BP and methylene chloride. Such method provides biodegradable microparticles which exhibit smooth, spherical morphology.

In certain embodiments, the biodegradable microparticles are manufactured using a method that evenly disperses the local anesthetic throughout the polymeric biodegradable microparticles.

The biodegradable microparticles are formulated to contain an effective amount of local anesthetic. "Effective amount" as used herein means the amount of local anesthetic needed to obtain the desired effect for treatment of pain or healing at the extraction site or other dental cavity or socket in need of treatment. In certain embodiments, the biodegradable microparticles may have a local anesthetic loading from about 5% to about 25% by weight of the biodegradable microparticle.

The biodegradable microparticles may be dispersed in the biodegradable hemostatic matrix by any means known in the art. Such methods include physical mixing of the biodegradable hemostatic matrix and the biodegradable microparticles. Dispersing the plurality of biodegradable microparticles in the biodegradable hemostatic matrix includes embedding, suspending or incorporating the microparticles into the biodegradable hemostatic matrix. The biodegradable microparticles are typically not chemically linked to the biodegradable hemostatic matrix, but rather are spatially confined (physically restricted) within the matrix until degradation thereof.

The biodegradable hemostatic matrix may comprise any hemostatic agent which is biodegradable, is capable of promoting blood clotting, slowing or stopping bleeding, and/or promoting healing, and is capable of allowing diffusion of the local anesthetic agent as released from the biodegradable microparticles through the biodegradable hemostatic matrix. The hemostatic matrix provides hemostatic properties, functions to spatially confine the biodegradable microparticles, and is permeable to diffusion of the local anesthetic agent such that the anesthetic agent is released into the tissue of a patient in which the biocompatible dental putty is placed.

Such hemostatic agents may include absorbable gelatin material such as bovine or porcine gelatin, microfibrillar collagen-type agents such as bovine collagen, or cellulosic agents such as oxidized regenerated cellulose. Nonlimiting examples of biodegradable hemostatic matrix material include Gelfoam®, an absorbable porcine gelatin, and Avitene®, a microfibrillar collagen material. In certain embodiments, the biodegradable hemostatic matrix comprises an absorbable porcine gelatin material.

In nonlimiting examples, the ratio of biodegradable microparticle to hemostatic matrix is 2:1, 1:1, or 1:2. In a preferred embodiment, the ratio of microparticles to matrix is 1:1.

Additional pharmaceutically active agents can be incorporated into the biocompatible dental putty delivering local anesthetics for extraction site administration. Such pharmaceutically active agents may include, e.g., antibiotics such as sulfisoxazole, penicillin G, ampicillin, cephalosporins, amikacin, gentamicin, tetracyclines, chloramphenicol, erythromycin, clindamycin, isoniazid, rifampin, and derivatives, salts and mixtures thereof; antifungals such as amphotericin B, nystatin, ketoconazole; antivirals such as acyclovir, amantadine, chlorahexidine; and other art known anti-infective.

Augmenting agents can also be included in the biocompatible dental putty according to the present disclosure. Such agents are compositions or compounds that may prolong the duration of local anesthesia and/or enhance the effectiveness of local anesthetic agents when delivered to the site of local anesthetic administration.

In certain embodiments of the disclosure, the augmenting agent can be from one or more of the following general types or classes of agents, including glucocorticosteroid agents, alkalinizing agents, non-glucocorticoid steroids such as, e.g., neuroactive steroids and/or steroid or nonsteroid modulators of gamma amino butyric acid ("GABA") receptors, modulators of ionic transport across cell membranes, including, e.g., modulators of membrane transport of monovalent and divalent metal ions such as, for example, blockers or enhancers of sodium, potassium and/or calcium transport across cell membranes, antipyretic agents, adrenergic receptor agonists or antagonists, such as α2 receptor agonists, tubulin binding agents, including, e.g., agents that are capable of either causing formation or disruption of intracellular microtubules, osmotic polysaccharides, agonists and antagonists of potassium ATP channels, i.e., able to open or close potassium ATP channels, Na, K-ATPase inhibitors and enhancers, neurokinin antagonists, PLC (i.e., phosphatidylinositol-specific phospholipase C) inhibitors, inhibitors of leukocyte glucose metabolism and anti-convulsants. The augmenting agent can also be an analeptic, a tranquilizing agent, an antidepressant, an anti-seizure agent, leukotriene and prostaglandin agonists and inhibitors, phosphodiesterase agonists and inhibitors, e.g., based on cAMP, and combinations of any of the foregoing. The aforementioned types of augmenting agents may be used alone or in any mixture or combination of each such agent to provide effective augmentation of local anesthesia where desired.

Augmenting agents that are vasoconstrictor agents in sustained release form include, but are not limited to, catecholamines e.g., epinephrine, norepinephrine and dopamine as well as, e.g., metaraminol, phenylephrine, methoxamine, mephentermine, methysergide, ergotamine, ergotoxine, dihydroergotamine, sumatriptan and analogs, and alpha-1 and alpha-2 adrenergic agonists, such as, e.g., clonidine, guanfacine, guanabenz and dopa (i.e., dihydroxyphenylalanine), methyldopa, ephedrine, amphetamine, methamphetamine, methylphenidate, ethylnorepinephrine ritalin, pemoline and other sympathomimetic agents, including, active metabolites, derivatives and mixtures of any of the foregoing.

The size and shape of the biocompatible dental putty of the disclosure can be formed such that the dentist or other technician can place the dental putty formulation inside a dental cavity or dental socket. As used herein, "cavity" and "socket" refer to a space in the mouth of a patient, for example, formed from extraction of a tooth, but may also refer to any space in the mouth requiring pain control or healing suitable for treatment by the biocompatible dental putty of the disclosure. As used herein, "patient" refers to any animal to be treated using the biocompatible dental putty of the disclosure.

The dental material of the disclosure is malleable, such that it can be shaped like clay or putty into a form suitable for placement in a dental socket and has appropriate cohesive properties for application and placement in the oral cavity of a patient. In certain embodiments, the dental putty is formed into a bolus, so that the bolus can be placed in the dental cavity or socket and conform to the surrounding tissue without leaving a pocket. In another embodiment, the dental putty may be formed to fill the cavity or socket sufficiently that surgical suturing is not needed and the bolus of local anesthetic becomes the closure means for the cavity or socket.

The biocompatible dental putty may be customized by molding for the size and/or shape of the dental socket for a particular patient. The biocompatible dental putty may also be customized as to the release profile of the local anesthetic agent in order to obtain the desired pain control, hemostatic effect, and healing for a patient after dental surgery.

In certain embodiments, the biocompatible dental putty comprises poly-(lactic-co-glycolic) (PLGA) microparticles containing bupivacaine (BP), the microparticles embedded within a polymeric hemostatic agent (i.e., matrix) to form a moldable putty. The formulation will enable oral surgeons to customize the delivery system to the size and shape of a patient's extraction site or cavity. As the cavity heals, the polymer and matrix dissolves, releasing the BP continuously. By coordinating the BP release kinetics with post-operative healing, pain can be controlled for days following surgery (FIG. 1).

In general, release of the anesthetic drug within the biocompatible dental putty is sustainable over the course of days within a site of tooth extraction. In certain embodiments, the time is 1 day, 2 days, 4 days, or 7 days.

The chemical and mechanical properties of the biocompatible dental putty are compatible with physiological conditions in a tooth extraction site. Conditions within a tooth extraction site generally include 37° C. and physiological pH. In one nonlimiting example, the drug is released from the biocompatible dental putty as the biodegradable microparticles degrade and diffuse through the biodegradable hemostatic matrix into the tissue of the tooth extraction site. Nonlimiting examples of mechanisms for microparticle degradation includes thermal degradation, oxidative degradation, and chemical degradation. In a preferred embodiment, a PLGA microparticle encapsulating local anesthetic agent hydrolytically degrades and releases the anesthetic agent.

In aspects of the disclosure, a pain management system is provided which is configured to be positioned in a dental extraction cavity in a patient after dental surgery. The pain management system comprises a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent. In certain embodiments, the biodegradable hemostatic matric is a porcine gelatin material, the biodegradable microparticles comprise PLGA and the local anesthetic agent comprises bupivacaine.

In one aspect of the disclosure, the biocompatible dental putty as disclosed herein may be provided in a dental kit. In such aspect, a dental kit is provided, comprising one or more units of a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent. In certain embodiments, the biodegradable hemostatic matric is a porcine gelatin material, the biodegradable microparticles comprise PLGA and the local anesthetic agent comprises bupivacaine. Each unit from the kit may be molded and customized for a particular patient.

In another aspect of the disclosure, a method of providing controlled release of a local anesthetic at a tooth extraction site in a patient in need of said local anesthetic is provided utilizing the biocompatible dental putty described herein. The method of providing controlled release of a local anesthetic comprises molding into a desired shape and size a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent; and applying the biocompatible dental putty to the tooth extraction site in the patient. In certain embodiments of the method of providing controlled release of a local anesthetic at a tooth extraction site, the biodegradable hemostatic matric is a porcine gelatin material, the biodegradable microparticles comprise PLGA and the local anesthetic agent comprises bupivacaine. The biocompatible dental putty may be configured to degrade completely and be absorbed into the body of the patient in less than 7 days, in less than 4 days, in less than 2 days, or in less than 1 day.

In a further aspect of the disclosure, a method of controlling pain in a patient after a tooth extraction is provided utilizing the biocompatible dental putty described herein. The method of controlling pain in a patient after a tooth extraction comprises molding into a desired shape and size a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent; and applying the biocompatible dental putty to the tooth extraction site in the patient. In certain embodiments of the method of controlling pain, the biodegradable hemostatic matric is a porcine gelatin material, the biodegradable microparticles comprise PLGA and the local anesthetic agent comprises bupivacaine. The biocompatible dental putty may be configured to degrade completely and be absorbed into the body of the patient in less than 7 days, in less than 4 days, in less than 2 days, or in less than 1 day.

EXAMPLES

Development of PLGA Microparticles

Initial formulations were prepared to determine which materials would provide sustainable release of local anesthetic. Formulations that exhibited sustainable BP release over three days in vitro were selected for subsequent preclinical assessment in a rodent model of tooth extraction. It was determined that application of selected formulations to molar extraction sites prevented the development of dental pain and corresponding changes in feeding behavior. These feasibility studies demonstrate the ability of extended release anesthetics to manage dental pain.

As part of the development effort, particle systems that encapsulated bupivacaine (BP) anesthetic were prepared. Solvent evaporation was used to encapsulate BP within PLGA microparticles (BP-PLGA microparticles). To support this approach, BP-HCl was first converted to the base form (BP-base), which is soluble in methylene chloride as required in the microparticle preparation method (FIG. 2A and FIG. 2B).

As shown, using PLGA with a molecular weight of 7-17 kDa, microparticles were generated that exhibited a smooth and predominantly spherical morphology with diameters between 1-20 µm. As shown by the SEM images (FIG. 3A and FIG. 3B), no appreciable morphological differences existed between BP-PLGA microparticles and microparticles without BP (i.e., drug-free PLGA microparticles).

Figure 4:
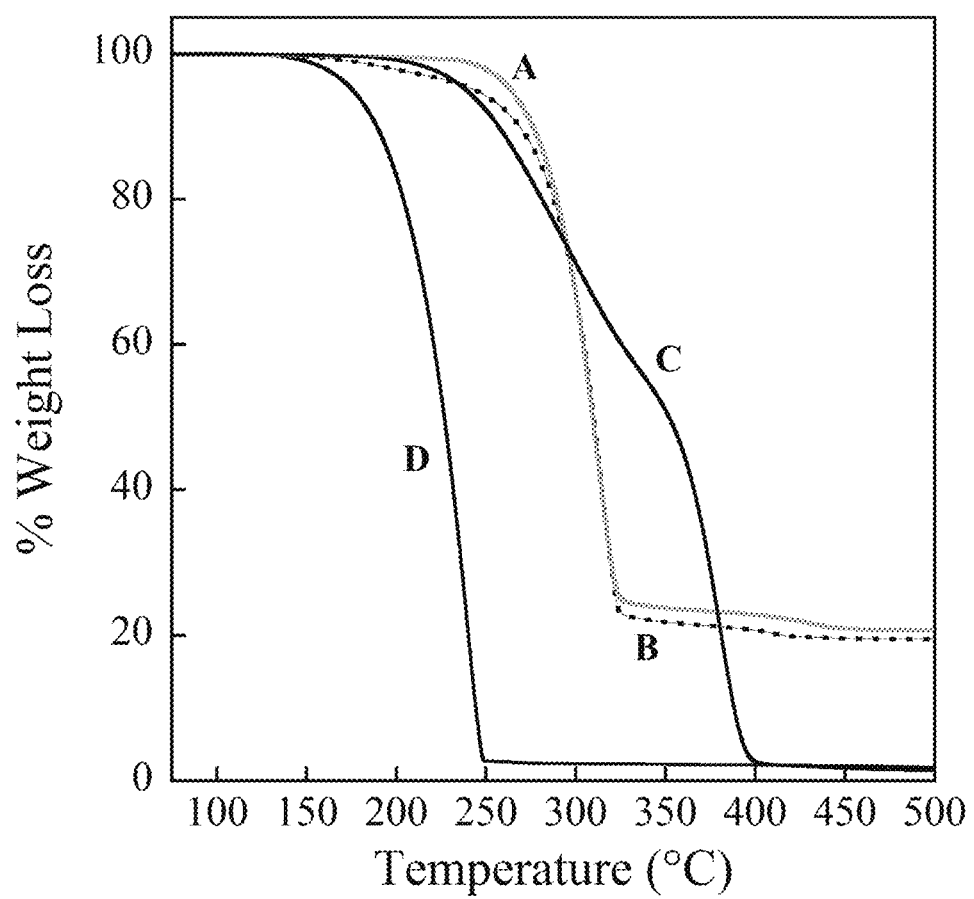
FIG. 4 is a graphical representation of TGA profiles showing % weight loss versus temperature for PLGA microparticles without BP (line A, grey line); BP-PLGA microparticles (line B, dashed line; PLGA polymer (MW 7-17 kDa) (line C); and BP-Base (line D). Each curve represents one TGA experiment.

To further characterize the samples, TGA studies were performed using the microparticles, the BP-Base, and the neat PLGA starting material. FIG. 4 is a graphical representation of the TGA profiles showing % weight loss versus temperature for line A, PLGA microparticles without BP (grey line), line B, BP-PLGA microparticles (dashed line), line C, PLGA polymer (MW 7-17 kDa) and line D, BP-Base. Each curve represents one TGA experiment.

For the microparticles, the TGA curves were similar between BP-PLGA microparticles and the drug-free PLGA microparticles; the weight loss plateaued at 19 wt %±2 wt % at 600° C. for both formulations. This plateau corresponds to the remaining NaCl in the formulations, in accordance with the salt content estimated during the synthesis procedure. However, the BP-PLGA microparticles showed an earlier drop in weight (5% weight loss at 240° C.), as compared to drug-free PLGA microparticles (1% weight loss at 240° C.). This drop in weight at 240° C. for BP-PLGA microparticles suggests loss of drug from the microparticles in agreement with the lower onset of decomposition temperature for BP-Base (210±2° C.). Neat PLGA starting material showed two regions in the decomposition profile suggesting the possibility of distinct degradation products.

To ascertain the BP loading efficiency, six replicate batches of BP-PLGA microparticles were prepared, washed, lyophilized, and subsequently quantified using ultra high performance chromatography (UHPLC). The drug loading of BP within the microparticles was 5 wt %±1 wt %, which is approximately a quarter of the theoretical drug loading capacity calculated in our protocol. This lower than anticipated loading efficiency may have resulted from various factors concerning formulation parameters (e.g., drug/PLGA ratio, content of emulsifier) and processing conditions (e.g., washing protocol, stirring speed, solvent evaporation rate). At 5% of BP, however, the loading efficiency was adequate for the targeted dosing requirements for the subsequent in vivo studies.

Development of PLGA Microparticles with Hemostat Material

To achieve a long-acting formulation for placement within an extraction site, BP-PLGA microparticles were combined with an absorbable hemostat material. Two clinical hemostat materials were evaluated: Avitene™, a collagen hemostat derived from bovine skin and Gelfoam® a hemostat derived from porcine skin gelatin. Although both hemostat materials readily combined with the PLGA microparticles through physical mixing, as shown in SEM images in FIG. 3C and FIG. 3D, rodents in the Gelfoam® group were quicker in returning to physiological baseline values, and consequently, Gelfoam® was selected for subsequent in vivo studies.

Figure 5:
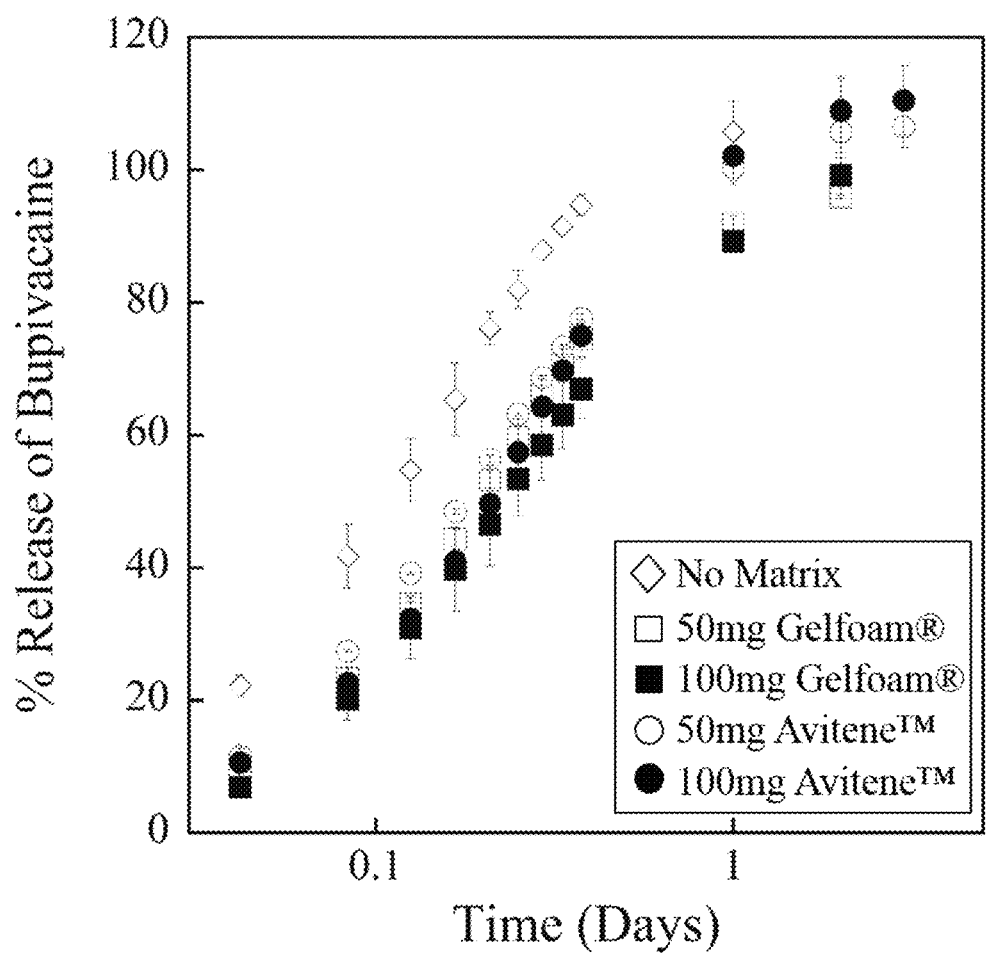
FIG. 5 is a graphical representation of the release of unencapsulated BP from matrix material. 1 mg of free BP-HCl in 0.9 wt/vol % NaCl was combined with either Gelfoam® or Avitene™ (at either 50 mg or 100 mg of matrix) and monitored for release through the matrix over time. The samples were placed in dialysis tubing and submerged in 1×PBS (pH=7.2) at 37° C.

Although the microparticles were not chemically linked to the hemostat, the hemostat was found to be capable of spatially confining the microparticles, while simultaneously allowing the diffusion of BP. To test the diffusion of free BP (i.e., not encapsulated in microparticles) through the hemostat, the material (i.e., free BP mixed with hemostat) was submerged in physiological media and the released BP measured over time. The hemostat materials did not impede the diffusion of BP, such that the majority of free BP was released from the hemostat over 24 hours (FIG. 5).

Early observations suggested that Gelfoam® held additional chemical advantages for these formulations. In particular, during incubation within physiological buffer, Avitene™ showed an extensive uptake of liquid as visually observed with extensive swelling of samples.

Example 1—Preparation of PLGA Microparticles Containing Bupivacaine

PLGA microparticles are prepared using a emulsion-solvent evaporation process. To enable dissolution of BP within methylene chloride for the solvent evaporation method bupivacaine hydrochloride monohydrate (Spectrum Chemical) was converted to the soluble base form. Briefly, 25 mL of a $NaHCO^{-3}$ solution (2.6 grams in 50 mL of $diH_2O$) was slowly added to a solution of 5 grams of BP-HCl in 150 mL of $diH_2O$. After allowing the solution to stand for approximately 10 minutes, the bupivacaine-base (BP-base) was extracted with dichloromethane three times (150 mL each), and dried over $MgSO_4$.

Solvent was then extracted via rotary evaporation and the resultant BP-base oil product was purified by precipitation and dried. Conversion results were verified via x-ray powder diffraction (XRD). The PLGA microparticles were prepared using an emulsion-solvent evaporation method.

In a typical procedure, a solution comprising (500 mg) of PLGA (Sigma, ester terminated, 50:50 ratio of lactic acid to glycolic acid, 7-17K Da), and (105 mg) of BP-base in (9 mL) of methylene chloride was added to 100 mL of Trizma®-buffered aqueous solution of 0.5% PVA (6000MW, Polysciences), and subsequently homogenized at ambient temperature using a handheld homogenizer for 60 seconds. The resultant emulsion was added to an additional 200 mL of 100 mM Trizma®-buffered $diH_2O$, and swirled to combine. The microparticles were introduced into a Buchi rotary evaporator at 45° C. for approximately 20 minutes ramping from 1000 mbar to 215 mbar, extracting the methylene chloride. The microparticles were spun down 2 times, removing supernatant in between, to concentrate the microparticles. Particles were subsequently resuspended and washed 2-times in saline, flash frozen, lyophilized, and stored until use at 4° C. Unless otherwise noted, all material was used as received without further purification.

Characterization of Microparticles and Materials

Measurement of BP Content in PLGA Particles.

To determine the content of BP in the microparticles, samples were first dissolved in acetonitrile and then quantified via HPLC. Residual NaCl in the formulations, which did not dissolve in acetonitrile, were weighed to approximate salt content.

XRD Analysis.

BP-Base and BP-HCl were analyzed with a Shimadzu XRD-600 instrument using a Bragg-Brentano geometry with a scintillation detector using a monochromator. The instrument used a copper anode as the source of radiation and analysis parameters of 0.04 degree two-theta steps for a dwell time of 4 seconds each step over a range of 8-70 degrees two-theta at power settings of 45 kV and 40 mA. The beam was conditioned through fixed divergence and scatter slits of 0.5 degree width and a receiving slit of 0.3 degrees width to maximize intensity and reduce background.

Thermogravimetric Analysis (TGA).

TGA was used to monitor mass changes in samples as the temperature was varied, which provides insight into the decomposition characteristics and content (e.g., NaCl content) of the material. TGA measurements were performed with a Q50 instrument from TA Instruments using a nitrogen gas ($N_2$) atmosphere at a ramp rate of 10° C./min from 25° C. to 600° C. All TGA measurements were performed in triplicate.

Scanning Electron Microscopy (SEM).

SEM images were acquired to examine morphology of the formulations. Samples were deposited on aluminum stubs, and sputter coated with a layer of gold/palladium, to create a charged surface. The particles were then examined using an FEI-brand SEM with an accelerating voltage between 5-15 kV under high vacuum.

Example 2—In Vitro Characterization of Formulation

In vitro release studies were performed using a dialysis method. Briefly, each sample was placed in dialysis tubing (Spectra/Por® Float-A-Lyzer®, cellulose ester, molecular weight cutoff of 8000-10,000) sealed, and incubated in physiological buffer (1×PBS, pH=7.2, Gibco) while being stirred at 37° C. For PLGA microparticle/matrix formulations, 40 mg of PLGA microparticles and 50 mg of Gelfoam® (Pfizer) were weighed into a small container and combined with 150 µL of $diH_2O$. Once combined, all PLGA microparticle/matrix formulations contained a final salt concentration of 0.9 wt % NaCl. For samples without matrix, 40 mg of PLGA microparticles were directly suspended with 1 mL of 1×PBS. In both cases, the ratio of BP-PLGA microparticles to non-BP-PLGA microparticles (40 mg total of microparticles) was varied to achieve predicted dosing of BP (Table 1).

TABLE 1

Formulations for controlled release of BP*

| Targeted Dosing (mg/kg/day) | Microparticle Ratio BP-PLGA: drug-free PLGA |
|---|---|
| 1 | 1:0 |
| 0.5 | 1:1 |
| 0.25 | 1:3 |
| 0 | 0:1 |

*Each formulation contained 40 mg microparticles + 50 mg Gelfoam ®

Figure 6:
FIG. 6 is a digital camera image of an exemplary dental putty including a hemostatic agent combined with PLGA microparticles which was manually molded into a bolus.

For all formulations that contained matrix (e.g., Gelfoam®, Avitene™ flour (Bard® Davol®)), samples were mixed by hand to form a moldable bolus, as shown in the exemplary digital camera image (FIG. 6).

Periodically, the dialysis tubing was transferred to fresh buffer preconditioned at 37° C. Samples were stored at 4° C. until ultra high performance chromatography (UHPLC) analysis. To assess diffusion of free drug through the matrix, 1 mg of unencapsulated BP (free-BP as the BP-HCl form) was added directly to either 50 mg or 100 mg of matrix.

UHPLC analysis of released BP was performed on a Waters (Milford, Mass.) ACQUITY UHPLC system equipped with a PDA detector set to 205 nm to quantify BP. A 0.10 mol/L phosphate buffer was prepared by dissolution of sodium dihydrogen phosphate monohydrate salt (98+%, ACS reagent, Sigma Aldrich, St. Louis, Mo.) and adjustment of the pH to 4.00 by addition of 1% HCl solution (concentrated HCl, Trace Metals Grade, Fisher Scientific, Hampton, N.H.). Acetonitrile (?99.9%, Sigma Aldrich) was used as the other eluent. Calibration standards were prepared by dissolution of solid BP acid and base form to produce stock solutions, which were then further diluted into acetonitrile to prepare the analytical standards at concentrations ranging from 0.68-55.5 µg/mL.

The acid form of BP was chromatographically separated on a Waters ACQUITY BEH C18 column (1.7 µm, 2.1×50 mm) by isocratic elution with 70% phosphate buffer/30% ACN at a flow rate of 0.60 mL/min. The base form of BP was chromatographically separated on a Waters ACQUITY UPLC HSS C18 SB column (1.8 µm, 2.1×50 mm) by isocratic elution with 55% phosphate buffer/45% ACN at a flow rate of 0.60 ml/min. Calibration standards were analyzed and the peaks corresponding to BP were integrated, plotted against the concentration, and the calibration curve was calculated by linear least-squares regression without weighting. Calibration standards were periodically reanalyzed to serve as quality control samples and monitor continuing system performance. The formulations showed sustained release of BP over the course of days.

Animals

Male and female Sprague Dawley rats, weighing between 200 g-430 g at the start of the experiment, were bred in-house from animals originally received from Charles River, N.C., USA. Rats of the same sex, and within the same treatment group, were pair housed for the duration of the study, and were maintained in a climate controlled facility under a 12-hour light/dark cycle. Rats had ad libitum access to water and food until the $3^{rd}$ day of the handling and habituation phase, at which point food was restricted per rat per day to 20 g Harlan Laboratory Chow (Harlan Teklad Global Rodent Diets, Wis.). This was determined to be in excess of the daily caloric requirement as outlined in the *Nutrient Requirements of Laboratory Animals* (1995 Fourth Revised Edition). All procedures were approved by the University of North Carolina at Chapel Hill's Institutional Animal Care and Use Committee, and adhered to the ARRIVE guidelines, the Guide for the Care and Use of Laboratory Animals (National Research Council. 2011; 8th Edition), and the Committee for Research and Ethical Issues of the International Association of the Study of Pain.

Food Preparation

Each cage housing a pair of rats was supplied, every 24 hours, with a total of 20 grams fresh feed in alternate sides of a dual food hopper, and 20 grams feed soaked in water and provided as a moist mush. The mush was placed in an appropriate receptacle, on the opposite side to the dry feed in the hopper, on the cage floor. Provision of the moist mush mimics current recommended standard of human care to eat soft food immediately following tooth extraction.

Surgical Procedure

The $1^{st}$ and $2^{nd}$ mandibular molars on the same facial side were extracted, with the side of extraction alternating between groups to control for chewing bias. Animals were anesthetized with an intraperitoneal (i.p.) injection of a 40 mg/mL ketamine hydrochloride (Mylan Industries LLC, IL, USA), 8 mg/mL xylazine (Lloyd Laboratories, IA, USA), and 0.5 mg/mL acepromazine maleate (Phoenix, Mo., USA) mix. Eyes were lubricated with an ophthalmic ointment (Altaire Pharmaceuticals, Inc., NY, USA) to prevent overdrying, a heat source was provided to prevent hypothermia, and 2 mL 0.9% sodium chloride (Baxter, Ill., USA) was administered subcutaneously (s.c.) as supportive therapy. Once a surgical plane of anesthesia was confirmed, 2 mg/kg bupivacaine (Hospira, Ill., USA) was administered s.c. in the facial area near the extraction site. Following this, the lip and tongue were gently pulled back with gloved fingers, and the gum carefully cut away from the molars with a #22 scalpel blade (Miltex, Germany). Once the roots were exposed, the teeth were loosened by being gently rocked backwards and forwards, and removed with a standard Blumenthal rongeur (World Precision Instruments, FL, USA). Blood and saliva were washed out of the mouth, the tooth socket dried as much as possible, and the hemostatic composite packed down into the socket.

In Vivo Gelfoam® Formulations

All formulations, with each respective vial containing enough material for 4 animals, were supplied as a lyophilized as a complex of Gelfoam®+microparticles by Research Triangle International (RTI, NC, USA). Five separate groups of males and females, with 4 animals per group, received one of the following formulation complexes: 1) Gelfoam® vehicle (GelVeh), 2) 2 mg/ml s.c. BP followed by Gelfoam® vehicle (BP+GelVeh), 3) 2 mg/ml s.c. BP followed by Gelfoam® complex with 1 mg/ml BP (BP+GelBP1™), 4) 2 mg/ml s.c. BP followed by Gelfoam® complex with 0.5 mg/ml BP (BP+GelBP.5™), and 5) 2 mg/ml s.c. BP followed by Gelfoam® complex with 0.25 mg/ml BP (BP+GelBP.25™). All samples were stored at 4° C., and prepared immediately prior to use in 600 ul 0.9% sodium chloride. The respective complexes were gently mixed with a plastic spatula (Fisherbrand™ Disposable Polypropylene Spatulas, USA), rolled into a ball between gloved fingers, and divided into four equal parts. Each ¼ was applied to a different animal in the same group.

Behavioral Phenotyping

Rats were handled and habituated to the testing environment for 4 days prior to the experiment. Food consumption, determined by weighing residual food in the cage, and body weight were measured prior to and on days 1-7 following molar extraction using a digital scale (Mettler Toledo, Ohio, USA).

Sensitivity to mechanical and thermal cold stimuli was determined prior to and on days 1, 2, 3, 5, and 7 following molar extraction, with measurements collected for both the treated side of extraction (ipsilateral) and untreated (contralateral) orofacial sites. The mechanical set-up was adapted from that established by Krzyzanowska (Krzyzanowska et al., "Assessing nociceptive sensitivity in mouse models of inflammatory and neuropathic trigeminal pain," *Journal of neuroscience methods,* 2011; 201:46-54). In brief, animals were loosely restrained by placing them in a regular housing cage, divided down the middle, where escape was prevented by setting the lid loosely on the cage (Tecniplast, Italy), thereby allowing free access to the vibrissal pads. Mechanical hyperalgesia was assessed using a 1.494 g von Frey filament. This filament was chosen, since it had a gram force value well over the 50% withdraw threshold for animals tested in the present study. The filament was applied to the vibrissal pad 10 times for a duration of 1 second, with an interstimulus interval of 1 second. The number of withdrawals (which could range from 0-10) was recorded at each time point. Mechanical hyperalgesia was defined as an increase in the number of withdrawals in response to a normally noxious mechanical stimulus.

Thermal cold sensitivity was measured, while gently hand-restraining the rat, by placing a cryostim probe maintained at 4° C., to the vibrissal pad for a maximum of 20 seconds, or until the rat withdrew from the stimulus. Withdrawal latencies were recorded in duplicate on ipsilateral and contralateral sides. If the second latency recorded was not within ±4 seconds of the first, a third measure was recorded. The 2 latencies closest in value were averaged in order to determine overall latency to withdrawal. Thermal hyperalgesia was defined as a decrease in withdrawal latency in response to the cryostim probe.

3. Statistical Analyses

Behavioral phenotyping data were analyzed by 2-way analysis of variance (ANOVA) to examine group differences over time. Mechanical and thermal sensitivity data were further analyzed by 1-way ANOVA to evaluate group differences on day 1 following tooth extraction, as this was the time of peak hyperalgesia. Post-hoc comparisons were performed using the Tukey's test correcting for multiple comparisons. For all analyses, statistical significance was defined as $P \leq 0.05$. All statistical analyses were performed using GraphPad Prism (GraphPad Prism Software, CA, USA).

Results and Discussion

Development and Characterization of Sustained Release BP Formulations

Various approaches exist to fabricate PLGA microparticles for controlled release of drugs, including spray drying, supercritical fluids technology, and solvent evaporation. The choice of method typically depends on the physicochemical properties of selected drug, requirements for efficiency of encapsulation, ease of methodology, scale-up, and cost. The solvent evaporation method was used in the examples herein to encapsulate BP within PLGA microparticles (BP-PLGA microparticles) (Zhang et al., "Bupivacaine-loaded biodegradable poly(lactic-co-glycolic) acid microspheres: I. Optimization of the drug incorporation into the polymer matrix and modelling of drug release" *Int. J. Pharm.,* 2008; 351: 244-9). To support this approach, BP-HCl was first converted to the base form (BP-base), which is soluble in methylene chloride.

A series of in vitro studies were performed to further understand the release kinetics of BP from microparticles. Using the dialysis method, samples were added to dialysis tubing, submerged in physiological buffer (1×PBS at pH 7.2) at 37° C., and the buffer was periodically quantified for release of BP. Four formulations were developed, with each formulation containing a specific weight ratio of BP-PLGA microparticles to drug-free PLGA particles, which were combined with Gelfoam (see Table 1 above). To accommodate the approximate volume within a dental cavity of a rat, a total of 40 mg of microparticles and 50 mg of Gelfoam® were combined, resulting in a total quantity of BP at 1.4 mg, 0.7 mg, 0.35 mg, and 0 mg.

Figure 7:
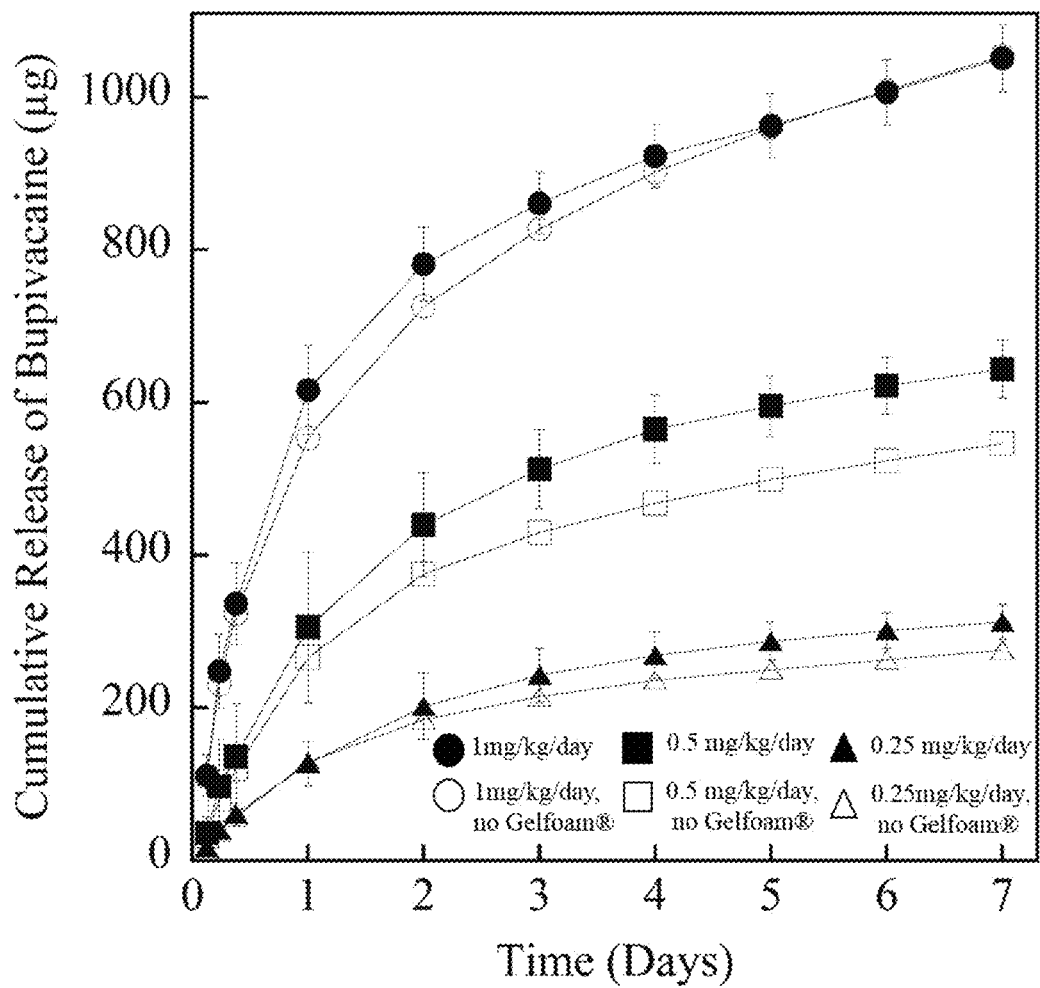
FIG. 7 is a graphical representation of in vitro release of BP from PLGA microparticles+Gelfoam® (filled markers) or PLGA microparticles without Gelfoam® (open markers). All samples were incubated at 37° C. in 1×PBS pH=7.2. Experiments containing the PLGA particles in Gelfoam® were performed in triplicate.

FIG. 7 shows the BP release profiles over time for each formulation. The corresponding samples without Gelfoam® were also tested to evaluate the effect of Gelfoam on the BP release kinetics. The graph shows that BP was similarly released from PLGA microparticles, irrespective of the presence of Gelfoam. No BP was detected in the negative control formulation (without BP) and was not included in the graph. As previously reported, the release of BP followed a biphasic pattern; the microparticles exhibit higher release within the first 24 hours, followed by subsequent tapering of release kinetics. For example, at 24 hours 24±4%, 19±10%, and 17±4% of BP was released from targeted dosing formulations of 1 mg/kg/day, 0.5 mg/kg/day, and 0.25 mg/kg/day, respectively. After 5 days, a total of 69±3%, 85±5%, and 82±6% of BP was released from targeted dosing formulations of 1 mg/kg/day, 0.5 mg/kg/day, and 0.25 mg/kg/day, respectively. The release profiles in FIG. 7 are compatible with the potential need for higher dosing of BP immediately post-surgery, when dental pain is prominent, and the requirement for less drug as the healing process begins.

In Vivo Studies

Figure 8:
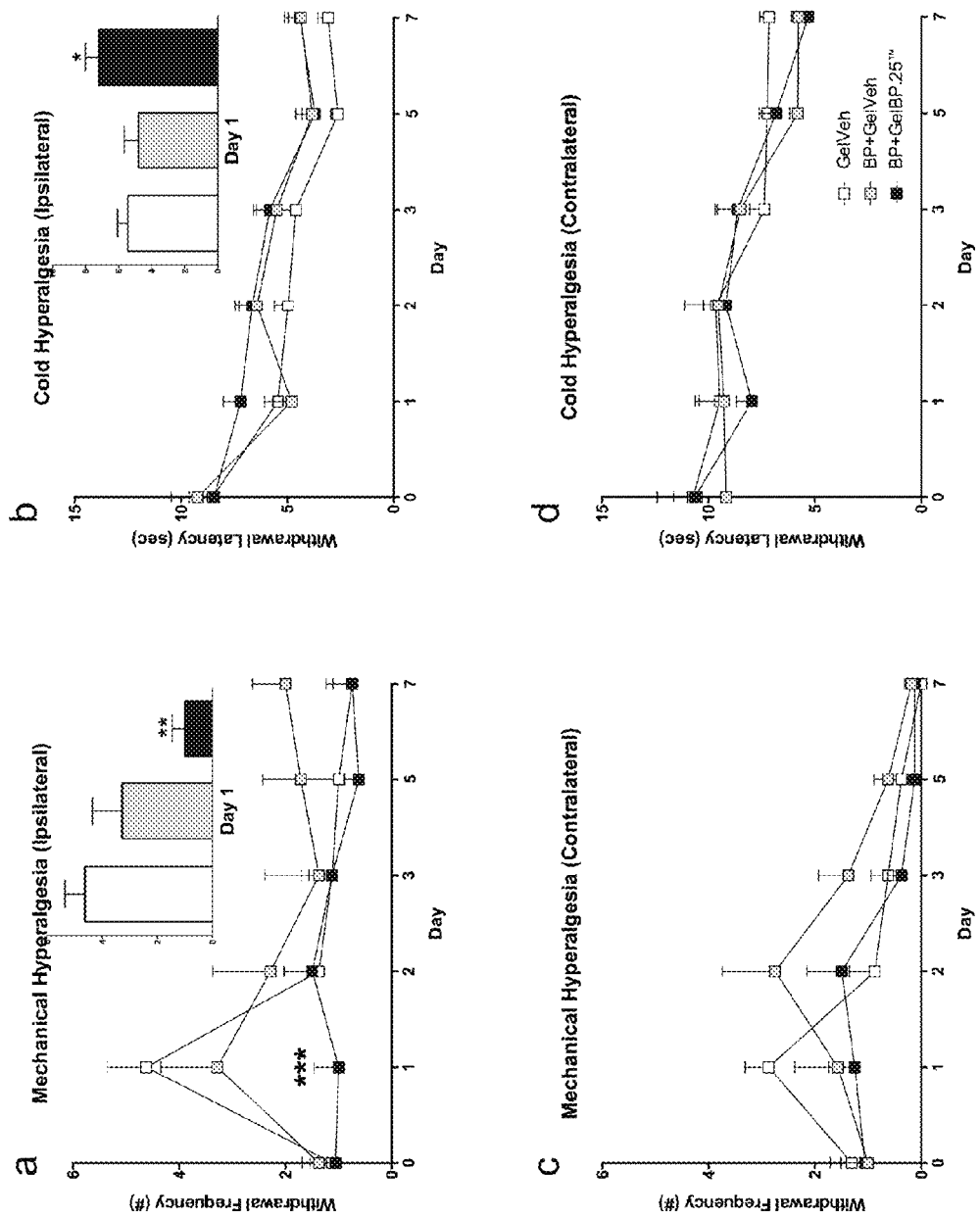
FIG. 8 is a set of graphical representations a-d of test results on rats of exemplary formulations of the disclosure and comparative formulations. As shown, GelBP outperforms acute BP in blocking post-surgical dental pain. Following tooth extraction, rats in the GelVeh control group exhibited mechanical hyperalgesia (a) and cold hyperalgesia (b), that peaked on day 1 following surgery. Administration of BP+GelBP.25™, but not BP+GelVeh, prevented hypersensitivity to mechanical and thermal stimuli. A trend towards contralateral mechanical sensitivity was observed among rats receiving GelVeh or BP+GelVeh on day 1 or day 2, respectively, but not among those receiving BP+GelBP (c). No differences in contralateral cold sensitivity were observed between groups at any time point (d). Data are expressed as mean±SEM. *$P \leq 0.05$, $P \leq 0.01$, and *$P \leq 0.001$ different from GelVeh.

The molar extraction procedure produced hypersensitivity to mechanical pressure and thermal cold. Behavioral responses were similar in males and females, so data were pooled. Rats in the GelVeh control group exhibited a 4-fold increase in withdrawal frequency to a punctate mechanical stimulus applied to the vibrissal pad ipsilateral to the tooth extraction site on day 1, indicative of mechanical hyperalgesia (FIG. 8, graph a). Mechanical hyperalgesia was completely blocked by the BP+GelBP.25 treatment, but not by BP+GelVeh ($F_{(2,21)}=5.370$, $P<0.01$). Rats in the GelVeh control group also exhibited a 5 second decrease in withdrawal latency to a thermal cold stimulus applied to the vibrissal pad ipsilateral to the tooth extraction site on day 1, indicative of cold hyperalgesia (FIG. 8, graph b). Cold hyperalgesia was blocked by the BP+GelBP.25 treatment, but not by BP+GelVeh ($F_{(2,21)}=3.296$, $P=0.05$).

A trend towards contralateral mechanical sensitivity was observed among rats receiving GelVeh or BP+GelVeh on day 1 or day 2, respectively, but not among those receiving BP+GelBP (FIG. 8, graph c). No differences in contralateral cold sensitivity were observed between groups at any time point (FIG. 8, graph d).

Figure 9:
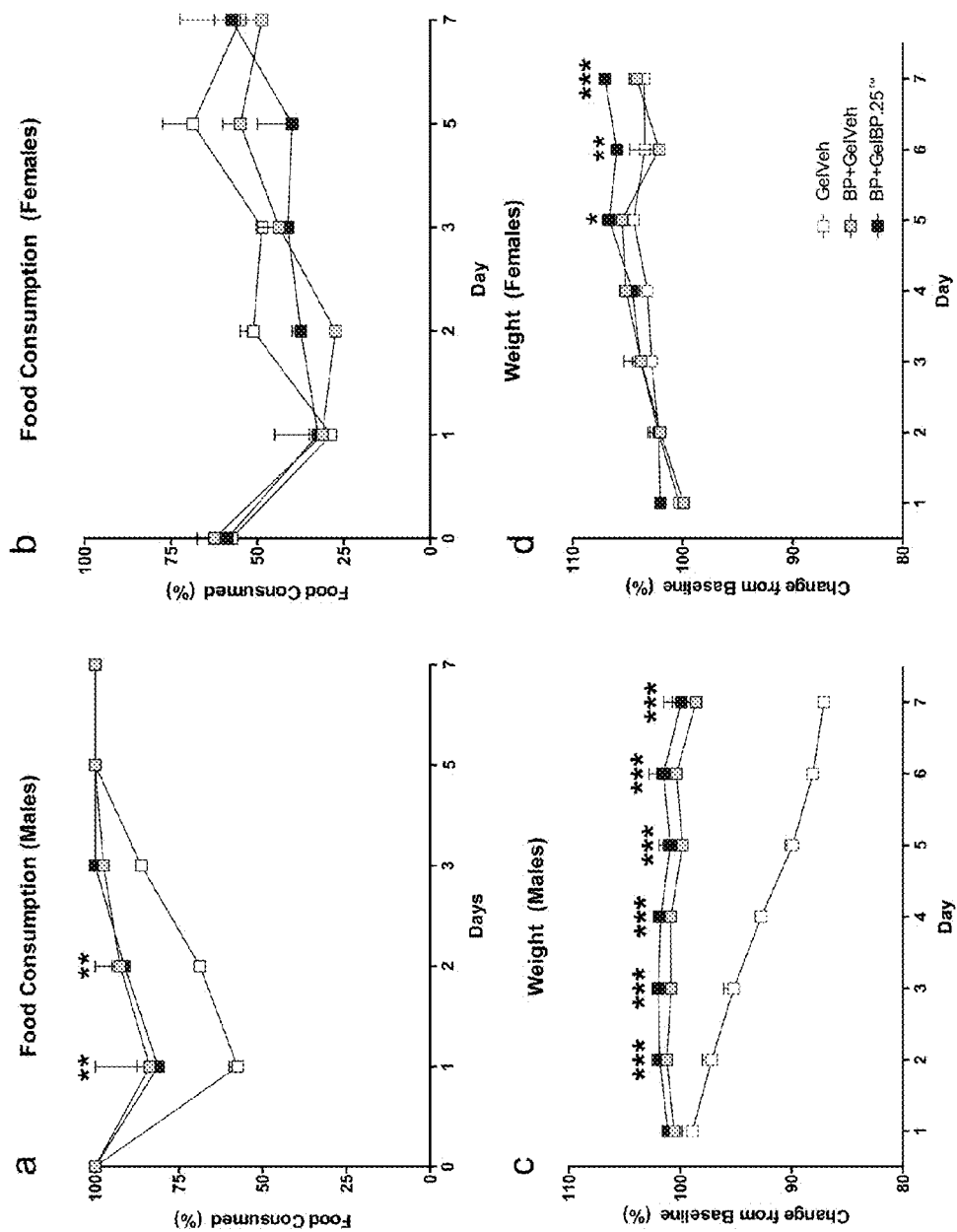
FIG. 9 is a set of graphical representations a-d of test results on rats of exemplary formulations of the disclosure and comparative formulations. As shown, GelBP improves food consumption and weight following tooth extraction. Male (a) and female (b) rats receiving only GelVeh prior to tooth extraction exhibited decreased food consumption. Males receiving BP+GelBP.25 or BP+GelVeh maintained normal food consumption throughout the 7-day testing paradigm, though significant group differences were not observed in females. Among males, those receiving BP+GelBP.25 or BP+GelVeh maintained normal weight throughout the 7-day period (c). Among females, only those receiving BP+GelBP.25 maintained weight on days 5-7 (d). Data are expressed as mean±SEM. $P \leq 0.01$ and *$P < 0.001$ different from GelVeh.

The molar extraction procedure produced a ~40% decrease in food consumption in males (FIG. 9, graph a) and females (FIG. 9, graph b) in the GelVeh control group on day 1, which normalized by day 5. Decreased food consumption was associated with corresponding reductions in weight for males on days 2-7 (FIG. 9, graph c), and to a lesser extent, females on days 6-7 (FIG. 9, graph d). Of the three GelBP doses applied, optimal results were achieved with the lowest GelBP.25 dose. Among males, those receiving BP+GelBP.25™ or BP+GelVeh failed to exhibit alterations in food consumption ($F_{(6,18)}$=9.45, P<0.002) or weight ($F_{(6,18)}$=49.93, P<0.0001) throughout the 7-day testing paradigm compared to those receiving GelVeh. Among females, those receiving BP+GelBP.25™ treatment exhibited greater weight gain on days 5-7 compared to those receiving GelVeh or BP+GelVeh ($F_{(6,18)}$=3.04, P<0.04), though no differences were observed in food consumption.

The examples support a novel platform for sustained delivery of anesthetic drug using drug-loaded microparticles embedded within a hemostat matrix. The formulation comprises a moldable putty for customized placement within an extraction site and continuous delivery of BP to prevent post-operative dental pain over the course of several days. To the extent known, this is the first demonstration of a tailorable anesthetic formulation designed for an extraction cavity during management of post-operative dental pain. This or a similar platform design may be used in conjunction with alternative active pharmaceutical agents and/or to alternative tissue sites. For example, microparticles embedded in gel could be loaded with antibiotics or vasoconstrictor agents and applied to extraction sites to prevent infection and promote healing. Additionally, this platform design could be adapted for delivery of anesthetic agents to other sites, such as topical wounds.

This disclosure describes a new formulation for treatment of dental pain comprising BP-PLGA microparticles, which were embedded within a hemostat matrix material. Two hemostatic agents, Gelfoam® and Avitene™, were successfully combined with the BP-PLGA microparticles, but Gelfoam® was ultimately selected for subsequent in vivo studies based on physical properties and compatibility with the rat animal model. In vitro studies showed sustained release of BP, which exhibited faster release kinetics early in the experiment that tapered over seven days. Subsequent preclinical studies demonstrated that application of the GelBup.25 formulation to molar extraction sites prevented the development of post-surgical dental pain and corresponding reductions in weight loss. This new formulation for anesthesia that resides within an extraction socket for a sustained dosing regimen and hemostatic function offers a novel approach for controlling post-operative dental pain. The sustained release formulation of BP for customized packing within an extraction cavity developed may eliminate post-operative dental pain over several days, as needed.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the claimed is intended to be broadly construed and interpreted, as including all such variations, modifications and alternative embodiments, within its spirit and scope.

What is claimed is:

1. A biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent.

2. The biocompatible dental putty of claim 1, wherein the biodegradable hemostatic matrix comprises an absorbable gelatin material.

3. The biocompatible dental putty of claim 1, wherein the biodegradable hemostatic matrix comprises an absorbable porcine gelatin material.

4. The biocompatible dental putty of claim 1, wherein the biodegradable microparticles comprise a polymeric material capable of providing controlled release of the local anesthetic agent encapsulated therein.

5. The biocompatible dental putty of claim 3, wherein the biodegradable microparticles comprise (poly)lactic-co-glycolic acid).

6. The biocompatible dental putty of claim 5, wherein the local anesthetic agent comprises bupivacaine.

7. A pain management system configured to be positioned in a dental extraction cavity in a patient after dental surgery comprising a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent.

8. The pain management system of claim 7, wherein the biodegradable hemostatic matrix comprises an absorbable porcine gelatin material, the biodegradable microparticles comprise (poly)lactic-co-glycolic acid), and the local anesthetic agent comprises bupivacaine.

9. A dental kit comprising one or more units of the pain management system of claim 7.

10. A method of providing controlled release of a local anesthetic at a tooth extraction site in a patient in need of said local anesthetic, comprising:
    molding into a desired shape and size a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent; and
    applying the biocompatible dental putty to the tooth extraction site in the patient.

11. The method of claim 10, wherein the biodegradable hemostatic matrix comprises an absorbable gelatin material.

12. The method of claim 10, wherein the biodegradable hemostatic matrix comprises an absorbable porcine gelatin material.

13. The method of claim 10, wherein the biodegradable microparticles comprise a polymeric material capable of providing controlled release of the local anesthetic agent encapsulated therein.

14. The method of claim 12, wherein the biodegradable microparticles comprise (poly)lactic-co-glycolic acid).

15. The method of claim 14, wherein the local anesthetic agent comprises bupivacaine.

16. The method of claim 14, wherein the biocompatible dental putty degrades in less than 7 days.

17. A method of controlling pain in a patient after a tooth extraction comprising:
    molding into a desired shape and size a biocompatible dental putty comprising a biodegradable hemostatic matrix having biodegradable microparticles dispersed therein, said biodegradable microparticles encapsulating a local anesthetic agent, wherein the biodegradable microparticles upon biodegradation thereof release the local anesthetic agent into the biodegradable hemostatic matrix and wherein the biodegradable hemostatic matrix is permeable to diffusion therethrough of the released local anesthetic agent; and applying the biocompatible dental putty to the tooth extraction site in the patient.

18. The method of claim 17, wherein the biodegradable hemostatic matrix comprises an absorbable porcine gelatin material, the biodegradable microparticles comprise (poly)lactic-co-glycolic acid), and the local anesthetic agent comprises bupivacaine.

19. The method of claim 18, wherein the biocompatible dental putty degrades in less than 7 days.

20. The biocompatible dental putty of claim 1, wherein the biodegradable microparticles contain the local anesthetic agent at a loading of from about 5% to about 25% by weight of the biodegradable microparticle.

21. The biocompatible dental putty of claim 1, wherein the biodegradable microparticles comprise (poly)lactic-co-glycolic acid having a molecular weight in a range of from 7 to 17 kDa.

22. The biocompatible dental putty of claim 21, wherein the (poly)lactic-co-glycolic acid is ester-terminated.

23. The biocompatible dental putty of claim 1, wherein the biodegradable microparticles contain the local anesthetic agent in a base form.

24. The biocompatible dental putty of claim 1, wherein the biocompatible dental putty provides a biphasic release of the local anesthetic agent.

25. The biocompatible dental putty of claim 1, wherein:

the biodegradable microparticles contain the local anesthetic agent at a loading of from about 5% to about 25% by weight of the biodegradable microparticle;

the biodegradable microparticles comprise ester-terminated (poly)lactic-co-glycolic acid having a molecular weight in a range of from 7 to 17 kDa;

the biodegradable microparticles contain the local anesthetic agent in a base form; and the biocompatible dental putty provides a biphasic release of the local anesthetic agent.

26. The method of claim 10, wherein the biodegradable microparticles contain the local anesthetic agent at a loading of from about 5% to about 25% by weight of the biodegradable microparticle.

27. The method of claim 10, wherein the biodegradable microparticles comprise (poly)lactic-co-glycolic acid having a molecular weight in a range of from 7 to 17 kDa.

28. The method of claim 27, wherein the (poly)lactic-co-glycolic acid is ester-terminated.

29. The method of claim 10, wherein the biodegradable microparticles contain the local anesthetic agent in a base form.

30. The method of claim 10, wherein the biocompatible dental putty provides a biphasic release of the local anesthetic agent.

* * * * *

UNITED STATES PATENT AND TRADEMARK OFFICE
CERTIFICATE OF CORRECTION

PATENT NO. : 9,943,466 B1
APPLICATION NO. : 15/622238
DATED : April 17, 2018
INVENTOR(S) : Leah Marie Johnson et al.

It is certified that error appears in the above-identified patent and that said Letters Patent is hereby corrected as shown below:

In the Specification

Column 13, Line 35: "?99.9%" should be -- $\geq$99.9% --.

Page 1 of 1

Signed and Sealed this
Twenty-second Day of May, 2018

Andrei Iancu
*Director of the United States Patent and Trademark Office*